United States Patent [19]

Lang et al.

[11] Patent Number: 4,766,235

[45] Date of Patent: Aug. 23, 1988

[54] UNSATURATED CAMPHOR DERIVATIVES, PROCESSES FOR PREPARING THE SAME AND PHARMACEUTICAL AND COSMETIC COMPOSITIONS CONTAINING THE SAME

[75] Inventors: Gérard Lang, Epinay-sur-Seine; Braham Shroot, Antibes; Serge Forestier, Claye Souilly; Alain Lagrange, Chatou, all of France

[73] Assignee: Societe Anonyme dite: L'Oreal, Paris, France

[21] Appl. No.: 927,226

[22] Filed: Nov. 5, 1986

Related U.S. Application Data

[63] Continuation of Ser. No. 681,661, Dec. 14, 1984.

[30] Foreign Application Priority Data

Dec. 16, 1983 [LU] Luxembourg .......................... 85144

[51] Int. Cl.$^4$ ..................... C07C 69/76; C07C 103/22

[52] U.S. Cl. ................................. 560/051; 562/459; 564/169; 514/532; 514/545; 514/520; 546/184; 546/192; 546/225; 546/226

[58] Field of Search ...................... 560/51; 562/459; 564/169; 546/225, 226

[56] References Cited

PUBLICATIONS

Strickland, S., Cancer Research, 43, 5268–72, Nov. 83.
Goodman, D. S., The Retinoids, vol. 1, p. 270, 1984.
Strickland, S., Cell, vol. 15, 393–403, Oct. 1978.

*Primary Examiner*—Paul J. Killos
*Attorney, Agent, or Firm*—Cushman, Darby & Cushman

[57] ABSTRACT

Unsaturated camphor derivatives have an activity in the topical and systemic treatment of acne, psoriasis and other dermatological disorders.

2 Claims, No Drawings

UNSATURATED CAMPHOR DERIVATIVES, PROCESSES FOR PREPARING THE SAME AND PHARMACEUTICAL AND COSMETIC COMPOSITIONS CONTAINING THE SAME

This is a continuation of application Ser. No. 681,661 filed on Dec. 14, 1984.

The present invention relates to new unsaturated camphor derivatives, to processes for preparing them and to cosmetic and pharmaceutical compositions the same.

The new unsaturated camphor derivatives of the present invention exhibit an activity in the topical and systemic treatment of acne, psoriasis and other allergic and inflammatory dermatological disorders or diseases. They also exhibit antitumoral activity.

Moreover, they are also useful in the treatment of cutaneous and respiratory atopies.

The unsatsurated camphor derivatives according to the present invention can be represented by the following formula:

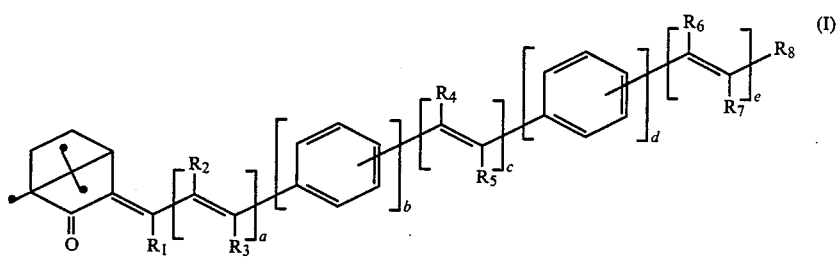

wherein, $R_1$ to $R_7$ each independently represent hydrogen, lower alkyl or trifluoromethyl, $R_8$ represents hydrogen, lower alkyl, lower alkoxy, aryl optionally substituted, $C\equiv N$, oxazolinyl or a radical corresponding to one of the following formulas:

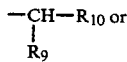 (i)

 (ii)

wherein
$R_9$ represents hydrogen, lower alkyl or $-OR_{14}$,
$R_{10}$ represents $$-N\begin{matrix}r'\\r''\end{matrix}$$

or $-OR_{14}$,
$R_{11}$ represents hydrogen, lower alkyl, $-OR_{15}$ or $$-(CH_2)_p-N\begin{matrix}r'\\r''\end{matrix}$$

wherein p is 0, 1, 2 or 3, r' and r" each independently represent hydrogen, alkyl, mono or polyhydroxyalkyl, alkenyl, cycloalkyl, aryl optionally substituted or aralkyl, or r' and r" together with the nitrogen atom to which they are attached form a heterocycle, or r' represents hydrogen and r" represents the residue or remainder of an amino acid or glucosamine, $R_{14}$ represents hydrogen, alkyl, alkanoyl, cycloalkyl or alkenyl, $R_{15}$ represents hydrogen, alkyl, mono or polyhydroxyalkyl, cycloalkyl, alkenyl, aryl, substituted aryl, aralkyl optionally substituted or the residue of a sugar, a, b, c, d and e represent 0 or 1, it being understood, on the one hand, that when b and/or d=1, $a+b+c+d+3\geq 2$ and on the other hand when b and d=0, $a+b+c+e=3$, and the optic and geometric isomers of the said compounds of formula I, as well as their salts with the exception of compounds of formula I wherein (1) $a+b+c+e=0$ and $d=1$, (2) $a+b+c=0$, $d=1$ and $e=1$ when $R_8$ represents

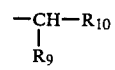

and

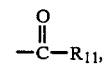

and (3) $a+b+e=0$, $c=1$ and $d=1$ and $d=1$ when $R_1$, $R_4$ and $R_5$ represent hydrogen and $R_8$ represents hydrogen, $-CH_2$ or $-OCH_3$.

By the term alkyl is meant, according to the present invention, radicals having from 1 to 20 carbon atoms, principally methyl, ethyl, propyl, 2-ethylhexyl, octyl, dodecyl, hexadecyl and octadecyl radicals.

By the term lower alkyl is meant, according to the present invention, radicals having from 1 to 6 carbon atoms, principally, methyl, ethyl, isopropyl, butyl and tert butyl radicals.

When the radicals $R_1$ to $R_7$ represent lower alkyl, methyl is preferred.

The lower alkoxy radical has from 1 to 4 carbon atoms, principally, methoxy, ethoxy or isopropoxy.

By the term aryl is meant phenyl optionally substituted by halogen such as chlorine, bromine or fluorine, hydroxyl or a nitro, lower alkoxy or amino group.

By the term alkenyl is meant a radical having 2 to 18 carbon atoms, principally propenyl, butenyl and isopentenyl radicals.

By the term cycloalkyl is meant a cyclopentyl or cylohexyl radical.

By the term monohydroxyalkyl is meant radicals having 2 or 3 carbon atoms, principally 2-hydroxyethyl and 2-hydroxypropyl.

By the term polyhydroxyalkyl is meant a radical having from 3 to 6 carbon atoms and 2 to 5 hydroxy groups, such as 2,3-dihydroxypropyl, 2,3,4-trihydroxypropyl and 2,3,4,5-tetrahydroxypentyl.

Representative aralkyl radicals include benzyl as well as phenethyl, optionally substituted by a hydroxyl function, an alkoxy group or a quaternary ammonium group.

When $R_{14}$ represents alkanoyl, it is preferably an acetyl or propionyl radical.

When r' and r" together form a heterocycle, the heterocycle can be piperidino, piperazino, morpholino or pyrrolidino.

By the expression "residue of a sugar" is meant a radical derived from a sugar such as glucose, mannitol or pentaerythritol.

When the compounds according to the present invention are provided in the form of salts, it is a question either of salts of an alkali metal or alkaline earth metal or of an organic amine when they carry at least one free acid function, or salts of a mineral or organic acid, principally hydrochlorides, hydrobromides or citrates when they carry at least one amine function.

Among the particularly preferred unsaturated derivatives according to the present invention, are those corresponding to the following formulas:

(A)                                                 (II)

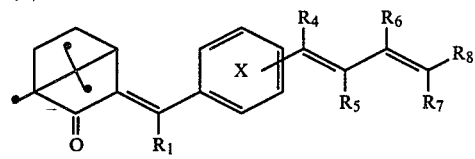

wherein
X represents the meta or para position on the aromatic ring,
$R_1$ represents hydrogen,
$R_4$ to $R_7$ each independently represents hydrogen or methyl, and
$R_8$ represents either

wherein
$R_{15}$ represents hydrogen, alkyl or a mono or polyhydroxyalkyl, or

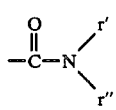

wherein r' represents hydrogen and r" represents alkyl, mono or poly-hydroxyalkyl, phenyl, phenyl substituted by hydroxy, or r' and r" together with the nitrogen atom to which they are attached form a piperdine ring;

(B)                                                 (III)

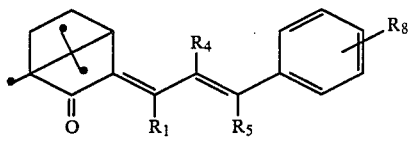

wherein
$R_1$ represents hyrogen or methyl,
$R_4$ and $R_5$ each independently represent hydrogen or methyl and
$R_8$ represents —$CH_3$ when at least one of $R_1$, $R_4$ and $R_5$ represents alkyl, or $R_8$ represents alkyl having 2 to 6 carbon atoms or

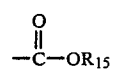

wherein $R_{15}$ represents hydrogen, alkyl or lower hydroxyalkyl, $R_8$ being in the para position on aromatic ring;

(C)                                                 (IV)

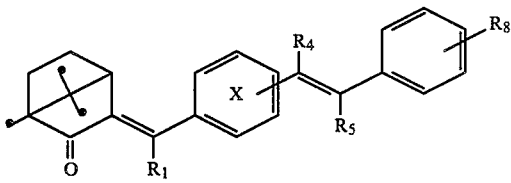

wherein
$R_1$ represents hydrogen,
$R_4$ and $R_5$ each independently represent hydrogen or methyl, and
$R_8$ represents

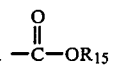

wherein $R_{15}$ represents hydrogen, alkyl or lower hydroxyalkyl, $R_8$ and X being in the meta or para position on the aromatic ring; and (D)                                                 (V)

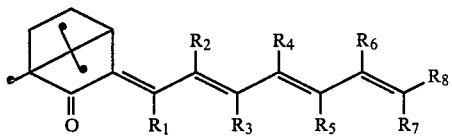

wherein
$R_1$ to $R_7$ each independently represent hydrogen or methyl and
$R_8$ represents

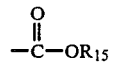

wherein $R_{15}$ represents hydrogen, alkyl or lower hydroxyalkyl.

Representative preferred compounds of formula II include the following:
(1) [4-ethoxy carbonyl-3-methyl-1E,3E butadiene]-4'-yl-3E benzylidene camphor,
(2) [4-ethoxy carbonyl-3-methyl-1E,3Z-butadiene]-4'-yl-3E benzylidene camphor,
(3) [4-ethoxy carbonyl-3-methyl-1E,,3E butadiene]-3'-yl-3E benzylidene camphor,
(4) [4-ethoxy carbonyl-1E,3E-butadiene]-4'-yl-3E benzylidene camphor,
(5) [4-ethoxy carbonyl-4-methyl-1E,3E-butadiene]-4'-yl-3E benzylidene camphor,
(6) [4-octadecyl oxycarbonyl-3-methyl-1E,3E-butadiene]-4'-yl-4E benzylidene camphor,
(7) [4-ethoxy carbonyl-1-methyl-1E,3E-butadiene]-4'-yl-3E benzylidene camphor,
(8) [4-ethoxy carbonyl-2-methyl-1E,3E butadiene]-4'-yl-3E benzylidene camphor,
(9) [4-carboxy-2-methyl-1E,3E butadiene]-4'-yl-3E benzylidene camphor,
(10) [4-carboxy-1E,3E butadiene]-4'-yl-3E benzylidene camphor,
(11) [4-carboxy-3-methyl-1E,3E butadiene]-4'-yl-3E benzylidene camphor,
(12) [4-carboxy-3-methyl-1E,3E butadiene]-3'-yl-3E benzylidene camphor,
(13) [4-carboxy-3-methyl-1E,3Z butadiene]-4'-yl-3E benzylidene camphor,
(14) [4-carboxy-1-methyl-1E,3E butadiene]-4'-yl-3E benzylidene camphor,
(15) [4-carboxy-4-methyl-1E,3E butadiene]-4'-yl-3E benzylidene camphor,
(16) [4-N-ethyl carbamyl-3-methyl-1E,3E butadiene]-4'-yl-3E benzylidene camphor,
(17) [4-piperidyl carbonyl-3-methyl-1E,3E butadiene]-4'yl-3E benzylidene camphor,
(18) [4-N-p-hydroxy phenyl carbamyl-4-methyl-1E,3E butadiene]-4'-yl-3E benzylidene camphor, and
(19) [2-N-hydroxy-4-ethyl carbamyl-3-methyl-1E,3E butadiene]-4'-yl-3E benzylidene camphor.

Representative preferred compounds of formula III include in particular:
(1) [4'methoxycarbonyl-3-phenyl-2-methyl-2E propene]3E-ylidene camphor,
(2) [3-p-tolyl-2-methyl-2E propene]-3E ylidene camphor,
(3) [3-p-tolyl-methyl-2E propene]-3E ylidene camphor, and
(4) [4'-carboxy-3-phenyl-2-methyl-2E propene]-3E ylidene camphor.

Representative compounds of formula IV include, in particular, the following:
(1) [4'ethoxy carbonyl-2-phenyl-1E ethene]-4'-yl-3E benzylidene camphor,
(2) [3'-ethoxy carbonyl-2-phenyl-1E ethene]-4'-yl-3E benzylidene camphor,
(3) [4'-ethoxy carbonyl-2-phenyl-2-methyl-1E ethene]-4'-yl-3E benzylidene camphor,
(4) [4'-ethoxy carbonyl-2-phenyl-1 methyl-1E ethene]-4'-yl-3E benzylidene camphor,
(5) [4'-carboxy-2-phenyl-1-methyl-1E ethene]-4'-yl-3E benzylidene camphor,
(6) [4'-carboxy-2-phenyl-1E ethene]-4'-yl-3E-benzylidene camphor, and
(7) [4'-carboxy-2-phenyl-2-methyl-1E ethene]-4'-yl-3E benzylidene camphor.

Representative compounds of formula V include in particular, the following:
[2,6-dimethyl-7 methoxy carbonyl-2E,4E,6E heptatriene]-3E ylidene camphor.

Various methods of synthesis can be employed to obtain the compounds of formula I; these methods are as follows:

A. First method.

This method consists in effecting a classic aldolic condensation of a compound of formula (1) on camphor (2) of natural or synthetic origin.

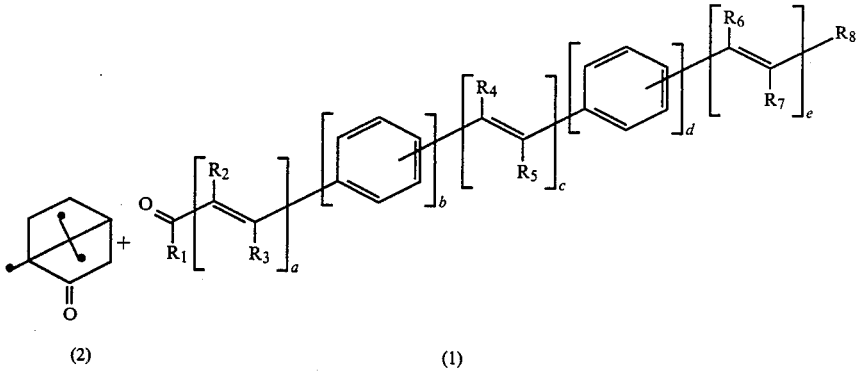

(2)  (1)

In accordance with this method, the various radicals of the compound of formula (1) can have the meanings given above for general formula I, $R_8$ not representing however

wherein $R_{11}$ represents hydrogen, alkyl or

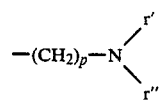

when $p \neq 0$.

The aldolic condensation can be carried out in a protic or aprotic solvent in presence of an organic base such as an alkaline alcoholate or a mineral base such as an alkaline amide or hydride, or a hydroxide of an alkali or alkaline said earth metal. This method is quite particularly appropriate for the synthesis of the compounds of formula III.

The compounds of formula (1) in which a+b+e=0, and c and d=1 can be prepared according to known methods, for example, by aldolic condensation of a compound of formula (3) on a compound of formula (4) in accordance with the following reaction scheme:

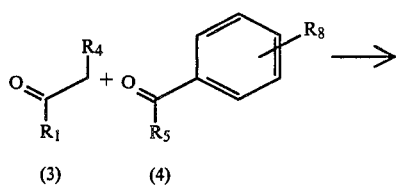

(3)   (4)

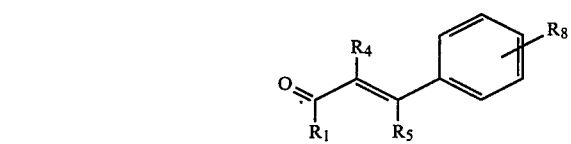

This aldolic condensation can be carried out under the same conditions as those described above.

B. Second method.

This method consists in condensing on the camphoroquinone (5), of d or l configuration or in the form of a mixture of d+l isomers, a compound of formula (6).

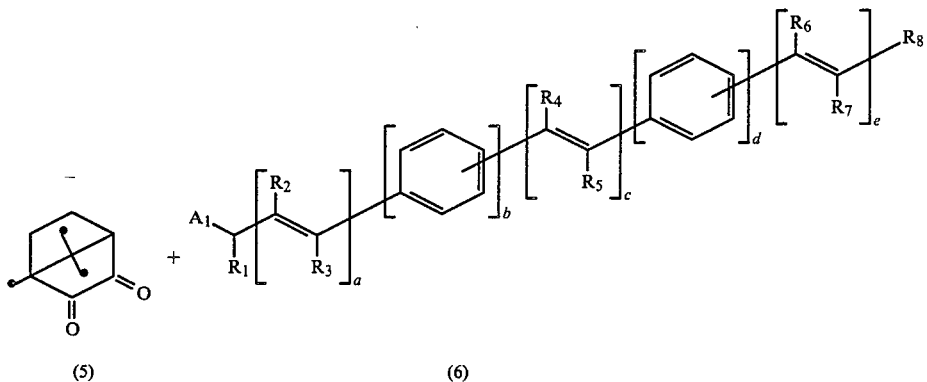

(5)                                    (6)

According to this method the various radicals of the compound of formula (6) can have the meanings given above for the general formula I, $R_8$ not representing

wherein $R_{11}$ represents hydrogen, alkyl or

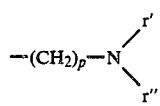

when $p \neq 0$.

$A_1$ represents either a triarylphosphonium group of the formula $-P[X]_3^{\oplus}Y^{\ominus}$, X being aryl and Y being an anion of an organic or inorganic acid, or a dialkoxyphosphinyl group of the formula

Z being an alkoxy.

When $A_1$ represents $-P[X]_3^{\oplus}Y^{\ominus}$, the condensation with the camphoroquinone (5) is carried out in the presence of an alkali metal alcoholate, such as sodium methylate or in the presence of an alkylene oxide optionally substituted by an alkyl group, the said condensation reaction optionally being carried out in a solvent such as methylene chloride or dimethylformamide. The temperature of the reaction is between ambient temperature and the boiling temperature of the reaction mixture.

When $A_1$ represents

the condensation with the camphoroquinone is carried out in the presence of a base and preferably in the presence of an inert organic solvent, for example, by means of sodium hydride in benzene, toluene, dimethylformamide or tetrahydrofuran, dioxane or 1,2-dimethoxy ethane or also by means of an alcoholate, for example, by means of sodium methylate in methanol, at a temperature ranging between 0° C. and the boiling point of the reaction mixture. The condensation can also be carried out by using a mineral base, such as NaOH or KOH, in an organic solvent such as tetrahydrofuran. A ring ether capable of complexing the metallic cation contained in the base can be added to the reaction mixture, thus permitting an increase in its strength. This method is quite particularly appropriate for the synthesis of compounds of formula V.

C. Third Method.

This method consists in condensing a compound of formula (7) on a compound of formula (8).

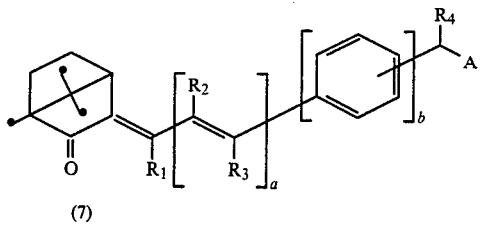

(7)

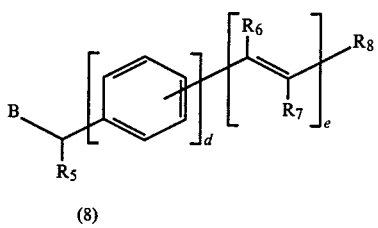

(8)

According to this method the various radicals of the compound of the formula (8) can have the meanings given above for the general formula I, $R_8$ not being able, however, to represent

$R_{11}$ representing hydrogen, alkyll or

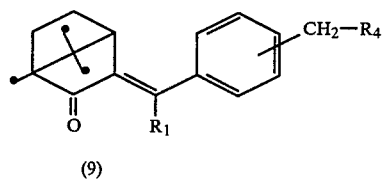

(9)

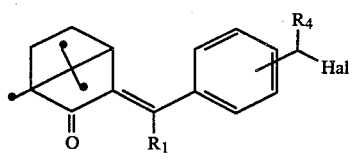

(10)

*Hal = Halogen $-(CH_2)_p-N\begin{matrix}r'\\r''\end{matrix}$ when p≠0.

In one of the formulas (7) or (8), A or B represents an oxo group and the other represents then either a triarylphosphonium group of the formula $-P[X]_3^\oplus Y^{63}$ or a dialkoxyphosphinyl group of the formula

$-P[Z]_2$,

X, Y and Z having the same meanings given above in the second method.

The consideration reaction conditions are the same as those described above for the second method as a function of the meanings of A and B.

This method is particularly appropriate for the synthesis of comouns of formula II and IV starting with a compound of formula (7) wherein A is $-P[X]_3^\oplus Y^\ominus$ or

$-P[Z]_2$ and a compound of formula (8) wherein B is an oxo group.

The compounds of formula (7) in which a=0 and b=1, A representing a triarylphosphonium group or a dialkoxy phosphinyl group can be prepared in accordance with the following reaction scheme:

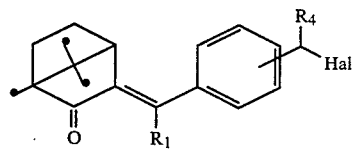

(10)

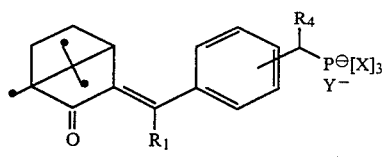

(11)

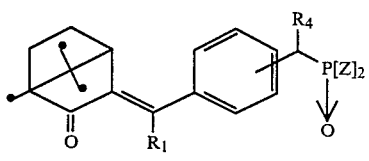

(12)

The halogenation of the compound of formula (9) can be effected in accordance with conventional procedures either by using chlorine or bromine, more particulary bromine, or by using a halogenating reactant such as the N-haloamides and more particularly the N-halosuccinimides such as N-bromo succinimide.

The halogenation is carried out in an inert organic solvent such as carbon tetrachloride in the presence of a radical initiator compound such as benzoyl peroxide or azobisisobutyronitrile and/or under UV irridation. The transformation of the halogen derivatives (10) into salts of triarylphosphonium of formula (11) or into dialkoxyphosphinyl derivatives of formula (12) can be carried out in accordance with known methods. In the triarylphosphonium salts the halide anion can ultimately be replaced by a $Y^\ominus$ anion.

The compounds of formula (8) in which B represents an oxo group can be obtained in accordance with conventional procedures.

D. Fourth Method.

This method consists in condensing a compound of general formula (13) with a compound of general formula (14).

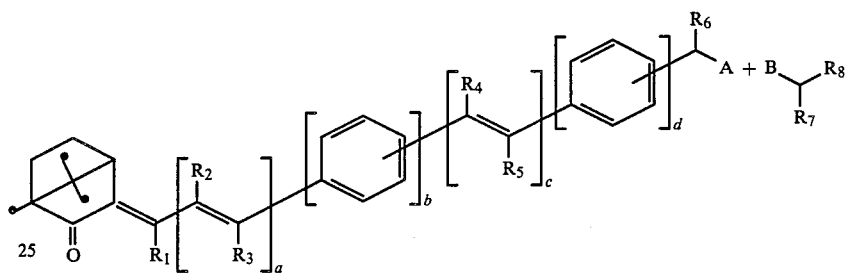

In one of the formulas (13) and (14), A or B represents an oxo group and the other then represents a triaryl phosphonium group of the formula $-P[X]_3^\oplus Y^\ominus$ or a group of the formula

When B represents the group $-P[X]_3^\oplus Y^\ominus$ or an oxo group, $R_8$ cannot represent the radical

when $R_{11}$ represents hydrogen, alkyl or

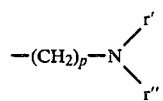

when $p \neq 0$.

When B represents

$R_8$ represents

$R_{11}$ representing $-OR_{15}$ or

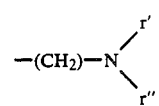

with $P \neq 0$.

The condensation reaction between compounds of formula (13) and (14) can be carried out under the same conditions as those described above for the second method of preparation as a function of the meanings of A and B.

This method is particularly appropriate for the preparation of compounds of formula III.

In this case the initial reactant has the following formula:

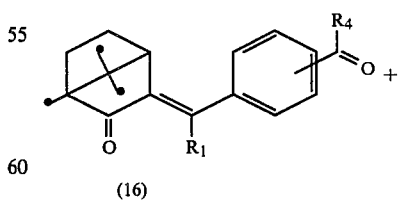

(15)

which can be obtained in accordance with one of the two following reaction schemes:

(1) Reaction scheme No. 1:

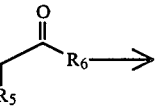

(16)

(17)

-continued

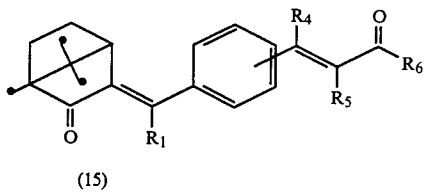

(15)

$R_6$ = H, $CH_3$, $C_2H_5$ or $CF_3$ (2) Reaction scheme No. 2:

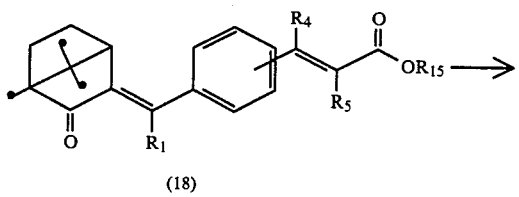

(18)

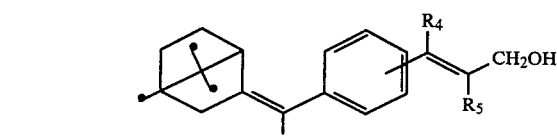

(19)

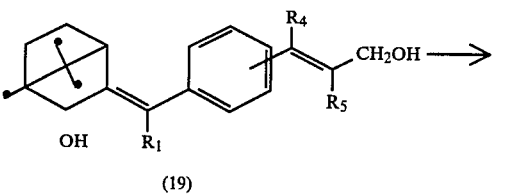

(19)

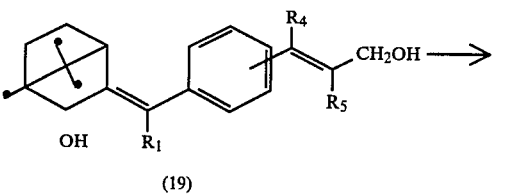

(15)

$R_6$ = H

In accordance with reaction scheme No. 1, the aldolic condensation of compound (16) on compound (17) can be carried out in a protic or aprotic solvent in the presence of an organic base such as an alkaline alcoholate or a mineral base such as an alkaline amide or hydride, or an alkali metal or alkaline earth metal hydroxide.

In accordance with reaction scheme No. 2, the reduction of compound (18) to compound (19) can be carried out using a metallic hydride, for example aluminum hydride and lithium-hydride. This reduction is carried out in an inert solvent at a temperature ranging between 0° C. and the boiling point of the solvent.

The oxidation of compound (19) to compound (15) ($R_6$=H) can be carried out by means of a mild oxidizing agent such as, for example, manganese dioxide in suspension in an inert solvent.

The following non-limiting examples illustrate the preparation of novel unsaturated camphor derivatives of the present invention.

EXAMPLE 1

Preparation of a compound of formula II wherein $R_1$, $R_4$, $R_5$ and $R_7$=H; $R_6$=$CH_3$; and $R_8$=—$CO_2C_2H_5$, X representing the para position.

(a1) 2.64 g of diethyl 3-ethoxycarbonyl-2-methyl-propen-2-yl phosphonate (mixture of cis/trans isomers in a 2/3 ratio) are added to a suspension of 1 g of pulverized potash in 30 cm³ of tetrahydrofuran. After 10 minutes of contact, 2.68 g of 3-d,1-benzlidene-4'-camphor carbaldehyde are added thereto. This reaction mixture is stirred for one hour at ambient temperature at which point it then is diluted with 100 cm³ of toluene. The reaction mixture is then filtered on celite and the filtrate is evaporated. After two recrystallizations in hexane, 2 g of product exhibiting the following characteristics are obtained:

Melting point: 118° C.
U.V. spectra (methanol): λ max: 358 nm, ε=52,450.

| Elemental analysis | C | H | O |
|---|---|---|---|
| Calculated | 79.33 | 7.99 | 12.68 |
| Found | 79.46 | 7.96 | 12.70 |

(a2) By chromatography of the filtrate of recrystallization under pressure (LOBAR column-Merck Silica-Eluant: hexane with 2.5% ethyl acetate and gradients up to 5% ethyl acetate) the isomer (1E, 3Z) is obtained:

Melting point: ≦50° C.
U.V. spectra (chloroform): λ max: 355 nm, ε=47,000.

| Elemental analysis | C | H | O |
|---|---|---|---|
| Calculated | 79.33 | 7.99 | 12.68 |
| Found | 79.13 | 7.95 | 12.82 |

(a3) In accordance wiht the same operating procedures described above, the 3-d,1-benzylidene-4'-camphor carbaldehyde is replaced with 3-d-benzylidene-4'-camphor carbaldehyde, the latter being obtained starting with natural camphor. The resulting product is purified by recrystallization in hexane.

Melting point: 143° C.
U.V. spectra (chloroform): λ max: 345 nm, ε=52,800.

| Elemental analysis | C | H | O |
|---|---|---|---|
| Calculated | 79.33 | 7.99 | 12.68 |
| Found | 79.52 | 7.97 | 12.60 |

EXAMPLE 2

Preparation of a compound of formula III wherein $R_1$ and $R_5$=H; $R_4$=$CH_3$ and $R_8$=p—$CO_2CH_3$ 3 g of camphor (2×10⁻² moles) in solution in 100 cm³ of 1,2-diemthoxy ethane are added at ambient temperature to a suspension of 0.96 g (2×10⁻² moles) of sodium hydride in 100 cm³ of 1,2-dimethoxy ethane under a nitrogen atmosphere. The reaction mixture is stirred for 2 hours then brought for 1 hour at reflux. The reaction mixture is then cooled to 0° C. at which point there is then slowly added a solution of 2 g (10⁻² moles) of 4-methoxycarbonyl-α-methyl cinnamaldehyde in 100 cm³ of 1,2-dimethoxy ethane. The resulting mixture is stirred for 5 hours during which period the temperature rises to 20° C. After destruction of the excess sodium hydride, the reaction mixture is poured into water and the product is extracted with hexane. 4 g of oil are obtained which is purified by chromatography on silica gel by using a mixture of hexane and ethyl acetate as eluant.

After evaporation of the solvent, 0.6 g of the expected product (yield: 18%) is obtained:
Melting point: 137° C.
U.V. spectra: (EtOH): λ max: 326 nm, ε=37,500.

| Elemental analysis | C | H | O |
|---|---|---|---|
| Calculated | 78.07 | 7.74 | 14.18 |
| Found | 78.13 | 7.75 | 14.02 |

EXAMPLE 3

Preparation of a compound of formula III wherein $R_1$ and $R_5$=H; $R_4$=CH$_3$; and $R_8$=p—CH$_3$ This compound is obtained in accordance with the same operating procedures as described in Example 2 except that the 4-methoxy carbonyl-α-methyl cinnamaldehyde is replaced by 4-dimethyl-α-cinnamaldehyde.

The resulting product is purified by recrystallization in a 9/1 ethanol-water mixture.
Melting point: 100° C.
U.V. spectra (EtOH): λ max: 324 nm, ε=31,800.

| Elemental Analysis | C | H | O |
|---|---|---|---|
| Calculated | 85.66 | 8.90 | 5.44 |
| Found | 85.52 | 8.84 | 5.62 |

EXAMPLE 4

Preparation of a compound of formula IV wherein $R_1$, $R_4$ and $R_5$=H; and $R_8$=p—CO$_2$C$_2$H$_5$, X designating the para position.

2.6 g of 3-benzylidene-4'-camphor carbaldehyde ($10^{-2}$ moles) and 3.2 g of diethyl 4-ethoxycarbonyl-benzyl phosphate ($10^{-2}$ moles) are dissolved in 20 cm$^3$ of tetrahydrofuran. This solution is then slowly added to a suspension of 0.5 g of sodium hydride in 20 cm$^3$ of tetrahydrofuran containing 0.06 g of 1,4,7,10,13-penta-oxo cyclopentadecane at 0° C. The temperature of the reaction mixture is permitted to rise to 20° C. and it is stirred for two hours. The reaction mixture is poured into water and the product is extracted with ether.

The product is purified by recrystallization in ethanol.
Melting point: 114° C.
U.V. spectra (EtOH): λ max: 356 nm, ε=59,600.

| Elemental analysis | C | H | O |
|---|---|---|---|
| Calculated | 81.12 | 7.29 | 11.58 |
| Found | 81.34 | 7.20 | 11.45 |

EXAMPLE 5

Preparation of a compound of formula II wherein $R_1$, $R_4$, $R_5$, $R_6$ and $R_7$=H and $R_8$=—CO$_2$C$_2$H$_5$, X designating the para position This compound is obtained in accordance with the same operating procedures described in Example 4 except that the diethyl 4-ethoxy carbonyl benzyl phosphonate is replaced by triethyl 4-phosphono-crotonate.

The resulting product is purified by recrystallization in ethanol.
Melting point: 110° C.
U.V. spectra (EtOH): λ max: 350 nm, ε=60,000.

| Elemental analysis | C | H | O |
|---|---|---|---|
| Calculated | 79.09 | 7.74 | 13.17 |
| Found | 78.91 | 7.73 | 13.20 |

EXAMPLE 6

Preparation of a compound of formula IV wherein $R_1$, $R_4$ and $R_5$=H and $R_8$=m—CO$_2$C$_2$H$_5$, X designating the para position.

This compound is obtained in accordance with the same operting procedures described in Exampl 4 except that the diethyl 4-ethoxycarbonyl benzylphosphonate is replaced by diethyl 3-ethoxycarbonyl benzylphosphonate.

The resulting product is purified by recrystallization in ethanol.
Melting point: 98° C.
U.V. spectra (methanol): λ max: 345 nm, ε=50,700.

| Elemental analysis | C | H | O |
|---|---|---|---|
| Calculated | 81.12 | 7.29 | 11.58 |
| Found | 80.95 | 7.30 | 11.75 |

EXAMPLE 7

Preparation of a compound of formula II wherein $R_1$, $R_4$, $R_5$, and $R_6$=H; $R_7$=CH$_3$ and $R_8$=—CO$_2$C$_2$H$_5$, X designating the para position (a) preparation of a compound of the formula:

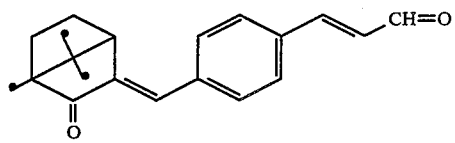

250 cm$^3$ of ether under argon are cooled to −30° C. and there are added thereto 3.8 g of lithium and aluminium hydride. At this temperature, there are then slowly introduced 33.8 g of [2-ethoxycarbonyl-1E-ethene]-4'-yl-3-E benzylidane camphor. The temperature of the reaction mixture is permitted to return slowly to ambient temperature at which point there are added thereto 100 cm$^3$ of ethyl acetate. The mixture is then diluted with water and filtered on celite. The organic phase is decanted and the solvent is distilled under reduced pressure.

The residue is dissolved in 160 cm$^3$ of ether and this solution is then added to a suspension of 50 g of manganese dioxide activated in 160 cm$^3$ of hexane. The resulting mixture is stirred for 2 hours as ambient temperature, then filtered and the solvent is evaporated.

The product is purified by chromatography on silica gel by using a 95:5 toluene-ethylacetate mixture as eluant. After evaporation the residue is recrystallized in isopropyl ether.
Melting point: 135° C.

| Elemental analysis | C | H | O |
| --- | --- | --- | --- |
| Calculated | 81.60 | 7.53 | 10.87 |
| Found | 81.54 | 7.60 | 11.05 |

(b) the same operating procedures described in Example 4 are repeated except that the 3-benzylidene-4'-camphor carbaldehyde is replaced by the compound obtained in part (a) above, and the diethyl 4-ethoxycarbonyl benzylphosphonate is replaced by triethyl 2-phosphono propionate.

The resulting products is purified by recrystallization in hexane.

Melting point: 120° C.

U.V. spectra (EtOH): λ max: 354 nm, $\epsilon$=59,200.

| Elemental analysis | C | H | O |
| --- | --- | --- | --- |
| Calculated | 79.33 | 7.99 | 12.68 |
| Found | 79.16 | 8.01 | 12.51 |

EXAMPLE 8

Preparation of a compound of formula III wherein $R_1$=CH$_3$; $R_4$ and $R_5$=H and $R_8$=p—CH$_3$ There is slowly added at 0° C. over a 10 minute period a solution of 2.42 g of diisopropylamine in 75 cm$^3$ of tetrahydrofuran to a solution of 0.022 mole of butyl lithium in hexane. After 15 minutes of stirring, the mixture is coded to −78° C., at which point there are added thereto 3.04 g of camphor in 25 cm$^3$ of tetrahydrofuran. The resulting mixture is stirred for 30 minutes at which point there is added thereto a solution of 3.52 g of 4-methyl benzalacetone in 20 cm$^3$ of tetrahydrofuran. This mixture is then stirred for 45 minutes at −78° C. and there is then added 62 cm$^3$ of normal HCl. The temperature is permitted to return to ambient temperature and the mixture is extracted three times with ether; the organic phase is washed with water and then dried on sodium sulfate. The solvent is distilled under reduced pressure. The residue is dissolved in 100 cm$^3$ of benzene. 0.1 g of paratoluene sulfonic acid is added thereto and the whole is brought to reflux for 90 minutes while distilling the water formed. The solvent is evaporated and the product is recrystallized in a 1:1 ethanol-hexane mixture, yielding 0.4 g of the anticipated product.

Melting point: 146° C.

U.V. spectra (EtOH): λ max: 338 nm, $\epsilon$=27,900.

| Elemental analysis | C | H | O |
| --- | --- | --- | --- |
| Calculated | 85.66 | 8.90 | 5.44 |
| Found | 85.50 | 8.75 | 5.75 |

EXAMPLE 9

Preparation of a compound of formula II wherein $R_1$, $R_4$, $R_6$ and $R_7$=H; $R_5$=CH$_3$ and $R_8$=—CO$_2$C$_2$H$_5$, X designating the para position.

(a) preparation of a compound of the formula:

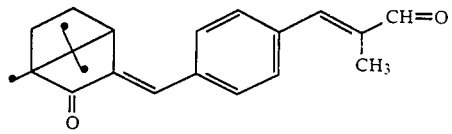

To a boiling solution of 0.3 cm$^3$ of soda at 30% in 10 cm$^3$ of methanol, a hot solution of 8 g of 3-benzylidene-4'-camphor carbaldehyde and 10 cm$^3$ of proponal in 70 cm$^3$ of methanol is slowly added. The resulting mixture is heated at reflux for one hour at which point the same is cooled and then poured into water. After extraction with ether and evaporation, there are obtained by recrystallization in isopropyl ether 3.7 g of pale yellow crystals.

Melting point: 114° C.

U.V. spectra (EtOH): λ max=328 nm, $\epsilon$=44,000.

| Elemental analysis | C | H | O |
| --- | --- | --- | --- |
| Calculated | 81.78 | 7.84 | 10.38 |
| Found | 81.60 | 7.83 | 10.52 |

(b) The same operating procedures as described in Example 4 are repeated except that the 3-benzylidene-4'-camphor carbaldehyde is replaced by the compound obtained in part (a) above and the diethyl 4-ethoxycarbonyl benzylphosphonate is replaced by triethyl phosphonoacetate.

The resulting produce is purified by recrystallization in hexane.

Melting point: 74° C.

U.V. spectra (EtOH): λ max=342 nm, $\epsilon$=45,500.

| Elemental analysis | C | H | O |
| --- | --- | --- | --- |
| Calculated | 79.33 | 7.99 | 12.68 |
| Found | 79.34 | 8.02 | 12.40 |

EXAMPLE 10

Preparation of a compound of formula II wherein $R_1$, $R_4$, $R_6$ and $R_7$=H; $R_5$=CH$_3$ and $R_8$=—CO$_2$H, X designating the para position.

1.5 g of the compound obtained in Example 9 are dissolved in 50 cm$^3$ of ethanol, to which are added 5 cm$^3$ of 3N NaOH. The mixture is heated at reflux for 30 minutes at which point 50 cm$^3$ of water are added and the alcohol distilled off. The reaction mixture is then acidified and the resulting product is filtered, washed with water, dried and recrystallized in ethylacetate.

Melting point: 208° C.

U.V. spectra (CHCl$_3$): λ max=344 nm, $\epsilon$=44,300.

| Elemental analysis | C | H | O |
| --- | --- | --- | --- |
| Calculated | 78.83 | 7.48 | 13.70 |
| Found | 78.96 | 7.54 | 13.54 |

EXAMPLE 11

Preparation of a compound of formula IV wherein $R_1$ and $R_4$=H; $R_5$=CH$_3$ and $R_8$=p—CO$_2$C$_2$H$_5$, X designating the para position.

This compound is obtained in accordance with the same operating procedures described in Example 4 except that the diethyl 4-ethoxycarbonyl benzylphosphonate is replaced by diethyl 4-ethoxycarbonyl phenylethyl phosphonate.

The resulting product is purified by recrystallization in ethanol.

Melting point: 134° C.
U.V. spectra (CHCl$_3$): λ max=336 nm, ε=44,100.

| Elemental analysis | C | H | O |
|---|---|---|---|
| Calculated | 81.12 | 7.29 | 11.58 |
| Found | 81.15 | 7.34 | 11.32 |

EXAMPLE 12

Preparation of a compound of formula IV wherein $R_1$ and $R_5$=H; $R_4$=CH$_3$ and $R_8$=p—CO$_2$C$_2$H$_5$, X designating the para position.

This compound is obtained in accordance with the same operating procedures described in Example 4 except that the 3-benzylidene-4'-camphor carbaldehyde is replaced by 4'-acetyl-3-benzylidene camphor.

The resulting product is purified by recrystallization in ethanol. A 25/75 mixture of E/Z isomers is obtained.

EXAMPLE 13

Preparation of a compound of formula IV wherein $R_1$ and $R_5$=H; $R_4$=CH$_3$ and $R_8$=p—CO$_2$H, X designating the para position.

This compound is obtained by hydrolysis of the compound obtained in Example 12 in accordance with the conditions set forth in Example 10.

The resulting product is purified by recrystallization in acetone.

Melting point: 230° C.
U.V. spectra (EtOH): λ max=325 nm, ε=26,700.

| Elemental analysis | C | H | O |
|---|---|---|---|
| Calculated | 81.00 | 7.00 | 12.00 |
| Found | 80.82 | 7.05 | 11.79 |

The product is provided in the form of a 25/75 mixture of E/Z isomers.

EXAMPLE 14

Preparation of a compound of formula IV wherein $R_1$, $R_4$ and $R_5$=H; and $R_8$=p—CO$_2$H, X designating the para position.

This compound is obtained by hydrolysis of the compound prepared in Example 4 in accordance with the same operating procedures described in Example 10.

The resulting product is purified by recrystallization in acetone.

Melting point: >260° C.
U.V. spectra (EtOH): λ max=356 nm, ε=56,000.

| Elemental analysis | C | H | O |
|---|---|---|---|
| Calculated | 80.83 | 6.74 | 12.44 |
| Found | 80.85 | 6.78 | 12.28 |

EXAMPLE 15

Preparation of a compound of formula II wherein $R_1$, $R_4$, $R_5$, $R_6$ and $R_7$=H and $R_8$=—CO$_2$H, X designating the para position.

This compound is obtained by hydrolysis of the compound obtained in Example 5 in accordance with the same operating procedures described in Example 10.

The resulting product is purified by recrystallization in acetone.

Melting point: 228° C.
U.V. spectra (EtOH): λ max=350 nm, ε=55,600.

| Elemental analysis | C | H | O |
|---|---|---|---|
| Calculated | 78.57 | 7.14 | 14.29 |
| Found | 78.51 | 7.22 | 14.30 |

EXAMPLE 16

Preparation of a compound of formula IV wherein $R_1$ and $R_4$=H; $R_5$=CH$_3$ and $R_8$=p—CO$_2$H, X designating the para position.

This compound is obtained by hydrolysis of the compound obtained in Example 11 in accordance with the same operating procedures described in Example 10.

The resulting product is purified by recrystallization in acetone.

Melting point: 265° C.
U.V. spectra (CHCl$_3$): λ max=336 nm, ε=41,200.

| Elemental analysis | C | H | O |
|---|---|---|---|
| Calculated | 81.00 | 7.00 | 12.00 |
| Found | 81.04 | 7.09 | 11.73 |

EXAMPLE 17

Preparation of a compound of formula III wherein $R_1$ and $R_5$=H; $R_4$=CH$_3$ and $R_8$=p—CO$_2$H.

This compound is obtained by hydrolysis of the compound obtained in Example 2 in accordance with the same operating procedures described in Example 10.

The resulting product is purified in recrystallization in acetone.

Melting point: 230° C.
U.V. spectra (EtOH): λ max=325 nm, ε=36,700.

| Elemental analysis | C | H | O |
|---|---|---|---|
| Calculated | 77.74 | 7.45 | 14.79 |
| Found | 77.73 | 7.51 | 14.65 |

EXAMPLE 18

Preparation of a compound of formula II wherein $R_1$, $R_4$, $R_5$ and $R_7$=H; $R_6$=CH$_3$ and $R_8$=—CO$_2$H, X designating the para position.

(a) This compound is prepared by hydrolysis of the compound obtained in Example 1 (a1) in accordance with the same operating procedures described in Example 10.

The resulting product is purified by recrystallization in acetone.

Melting point: 251° C.
U.V. spectra (EtOH): λ max=348 nm; ε=50,800.

| Elemental analysis | C | H | O |
|---|---|---|---|
| Calculated | 78.82 | 7.47 | 13.69 |
| Found | 78.76 | 7.53 | 13.70 |

(b) On hydrolysis of the (1E, 3Z) isomer obtained in Example 1 (a2) in accordance with the same operating procedures described in Example 10 the corresponding acid having the (1E, 3Z) structure is obtained.

The product is recrystallized in acetone.
Melting point: 244°–246° C.
U.V. spectra (methanol): λ max=348 nm; ε=46,600.

| Elemental analysis | C | H | O |
|---|---|---|---|
| Calculated | 78.82 | 7.47 | 13.69 |
| Found | 78.91 | 7.45 | 13.52 |

(c) On hydrolysis of the compound obtained in Example 1 (a3) in accordance with the same operating procedures described in Example 10, the corresponding optical isomer is obtained.

The product is purified by recrystallization in acetone.
Melting point: 238° C.
U.V. spectra (methanol—DMSO): λ max=341 nm, ε=52,300.

| Elemental analysis | C | H | O |
|---|---|---|---|
| Calculated | 78.82 | 7.47 | 13.69 |
| Found | 78.94 | 7.52 | 13.80 |

Rotary power: (chloroform) $[\alpha]_D = +570$

EXAMPLE 19

Preparation of a compound of formula II wherein $R_1$, $R_5$, $R_6$ and $R_7$=H; $R_4$=$CH_3$ and $R_8$=—$CO_2C_2H_5$, X designating the para position.

This compound is obtained in accordance with the same procedures described in Example 4 except that the 3-benzylidene-4'-camphor carbaldehyde is replaced by 4'-acetyl-3-benzylidene camphor and the diethyl 4-ethoxycarbonyl benzyl phosphonate is replaced by triethyl 4-phosphono crotonate.

EXAMPLE 20

Preparation of a compound of formula II wherein $R_1$, $R_5$, $R_6$ and $R_7$=H; $R_4$=$CH_3$ and $R_8$=$CO_2H$, X designating the para position.

The crude compound obtained in Example 19 is hydrolyzed in accordance with the same procedures described in Example 10.

The resulting product is purified by recrystallization in acetone.
Melting point: 228° C.
U.V. spectra ($CHCl_3$): λ max=345 nm; ε=40,500.

| Elemental analysis | C | H | O |
|---|---|---|---|
| Calculated | 78.83 | 7.48 | 13.70 |
| Found | 78.87 | 7.54 | 13.67 |

EXAMPLE 21

Preparation of a compound of formula II wherein $R_1$, $R_4$, $R_5$ and $R_7$=H; $R_6$=$CH_3$ and $R_8$=—$CO_2C_2H_5$, X designating the meta position.

This compound is obtained in accordance with the same procedures described in Example 1 except that the 3-benzylidene-4'-camphor carbaldehyde is replaced by 3-benzylidene-3'-camphor carbaldehyde.

The resulting product is purified by recrystallization in hexane.

EXAMPLE 22

Preparation of a compound of formula II wherein $R_1$, $R_4$, $R_5$ and $R_7$=H; $R_6$=$CH_3$ and $R_8$=—$CO_2H$, X designating the meta position.

This compound is prepared by hydrolysis of the compound obtained in Example 21 in accordance with the operating procedures described in Example 10.

The resulting product is purified by recrystallization in acetic acid.
Melting point: >250° C.
U.V. spectra (saturated solution in methanol) λ max=302 nm;

| Elemental analysis | C | H | O |
|---|---|---|---|
| Calculated | 78.82 | 7.47 | 13.69 |
| Found | 78.83 | 7.52 | 13.86 |

EXAMPLE 23:

Preparation of a compound of formula II wherein $R_1$, $R_4$, $R_5$ and $R_7$=H; $R_6$=$CH_3$ and $R_8$=—$CONHC_2H_5$, X designating the para position.

2 g of the compound obtained in Example 18(a) and 0.55 cm³ of phosphorus trichloride in 20 cm³ of toluene are stirred for 2 hours at ambient temperature and then distilled under reduced pressure. 100 cm³ of ether are then added and the reaction mixture is cooled to −30° C. at which point a solution of 1 cm³ of ethylamine in 50 cm³ of ether is added thereto. The mixture is then stirred for 3 hours at ambient temperature. The organic phase is washed with water. The solvent is distilled off under reduced pressure and the product is purified by chromatography on silica gel (eluant: dichloromethane, then a 50:50 mixture of dichloromethane and ethyl acetate), yielding 1.4 g of the expected product having the following characteristics:
Melting Point: 158° C.
U.V. spectra: λ max=349 nm, ε=52,800.

| Elemental analysis | C | H | N | O |
|---|---|---|---|---|
| (0.5 $H_2O$) Calculated | 77.62 | 8.28 | 3.62 | 10.35 |
| Founded | 77.62 | 8.34 | 3.66 | 10.18 |

EXAMPLE 24:

Preparation of a compound of formula II wherein $R_1$, $R_4$, $R_5$ and $R_7$=H; $R_6$=$CH_3$ and $R_8$=

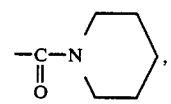

X designating the para position.

There is heated for 2 hours at 40° C. a suspension of 2 g of the compound obtained in Example 18(a) in 20 cm³ of toluene and 0.55 cm³ of phosphorus trichloride. The toluene is distilled off under reduced pressure. The residue is redissolved in 100 cm³ of ether to which is then added 0.6 cm³ of piperidine in solution in 30 cm³ of ether. The resulting mixture is stirred for 3 hours at ambient temperature. After dilution with water and extraction with ether, the product is purified by chromatography on silica gel (eluent: dichloromethane, then an 85:15 dichloromethane-ethyl acetate mixture).

After evaporation of the solvent, 0.6 g of the expected product is obtained.

Melting point: 140° C.

U.V. spectra (chloroform): λ max=348 nm, ε=49,600.

| Elemental analysis | C | H | N | O |
|---|---|---|---|---|
| Calculated | 80.53 | 8.44 | 3.35 | 7.66 |
| Found | 80.54 | 8.51 | 3.40 | 7.66 |

EXAMPLE 25:

Preparation of a compound of formula II wherein $R_1$, $R_4$, $R_5$ and $R_6$=H; $R_7$=CH$_3$ and $R_8$=—CO$_2$H, X designating the para position.

This compound is prepared by hydrolysis of the compound obtained in Example 7 in accordance with the same procedure described in Example 10.

The resulting product is purified by recrystallization in acetone.

Melting point: 240° C.

U.V. spectra (methanol-saturated solution): λ max=354 nm.

| Elemental analysis | C | H | O |
|---|---|---|---|
| Calculated | 78.83 | 7.48 | 13.70 |
| Found | 78.84 | 7.48 | 13.58 |

EXAMPLE 26:

Preparation of a compound of formula II wherein $R_1$, $R_4$, $R_5$ and $R_7$=H; $R_6$=CH$_3$ and $R_8$=

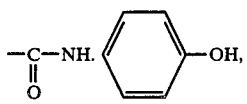

X designating the para position.

A suspension of 2.5 g of the compound obtained in Example 18(a) in 40 cm$^3$ of tetrahydrofuran and 0.53 cm$^3$ of thionyl chloride are stirred for 2 hours at ambient temperature. The solution is filtered and there is added to the filtrate a solution of 0.82 g of paraminophenol in 10 cm$^3$ of tetrahydrofuran. The mixture is then left at ambient temperature for 20 hours at which point it is diluted with 100 cm$^3$ of water. After acidification with 2N HCl, the product is extracted with dichloromethane. The organic phase is dried on sodium sulfate. The solvent is distilled under reduced pressure. The resulting product is purified by recrystallization in ethanol.

Melting point: 360° C.

U.V. spectra (methanol): λ max=360 nm, ε=69,600.

| Elemental analysis | C | H | N | O |
|---|---|---|---|---|
| Calculated | 79.06 | 6.86 | 3.17 | 10.89 |
| Found | 79.31 | 6.99 | 3.22 | 10.68 |

EXAMPLE 27:

Preparation of a compound of formula II wherein $R_1$, $R_4$, $R_5$ and $R_7$=H; $R_6$=CH$_3$ and $R_8$=—CONHCH$_2$CH$_2$OH, X designating the para position.

There are heated for 1 hour at 50° C., 3.5 g of the compound obtained in Example 18(a) and 1.6 g of carbonyldiimidazole in 200 cm$^3$ of dimethylformamide. The mixture is then cooled to 0° C. at which point there is added 0.7 cm$^3$ of monoethanolamine. The reaction mixture is then progressively heated to 70° C. and maintained at this temperature for 2 hours. There is then again added 0.7 cm$^3$ of monoethanolamine and the mixture is continued to be heated for 1 hour. The dimethylformamide is distilled off under reduced pressure and then diluted with water. The mixture is extracted with ethyl acetate. After evaporation of the solvent and purification by chromatography on silica gel, 1:4 g of a light oil are obtained which crystallizes in ethyl acetate. The resulting product exhibits the following characteristics:

Melting point: 138° C.

U.V. spectra (CHCl$_3$): λ max=352 nm, ε=46,000.

| Elemental analysis | C | H | N | O |
|---|---|---|---|---|
| (0.25 H$_2$O) Calculated | 75.69 | 8.26 | 3.58 | 12.90 |
| Found | 75.47 | 7.92 | 3.52 | 13.08 |

EXAMPLE 28:

Preparation of a compound of formula II wherein $R_1$, $R_4$, $R_5$ and $R_7$=H; $R_6$=CH$_3$ and $R_8$=

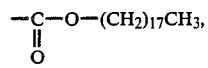

X designating the para position.

There are heated at 80° C. for 2 hours 3.5 g of the compound obtained in Example 18(a) and 1.8 g of carbonyldiimidazole in 50 cm$^3$ of dimethylformamide.

The mixture is then cooled to 0° C. at which point there are added 3 g of 1-octadecanol and 1.7 g of 1,8-diaza-7-becyclo[5.4.0]undecene. The mixture is then stirred for 4 hours and then diluted with 200 cm$^3$ of isopropyl ether. The organic phase is washed with 2N HCl, then with water and finally with a saturated solution of potassium carbonate. The solvent is distilled under reduced pressure. The residue is redissolved in 100 cm$^3$ of hexane and the solution is filtered. The crude product is purified by chromatography on silica gel (eluant: 95:5 hexaneethyl acetate mixture). A first fraction (1 g) of the 1E,3Z isomer having the following characteristics is obtained:

Melting point: 78° C.

U.V. spectra (chloroform): λ max=354 nm, ε=47,250.

| Elemental Analysis | C | H | O |
|---|---|---|---|
| Calculated | 81.67 | 10.36 | 7.96 |
| Found | 81.66 | 10.39 | 8.25 |

The second fraction (1.8 g) is the 1E,3E isomer having the following characteristics:

Melting point: 80° C.

U.V. spectra (chloroform): λ max=352 nm, ε=54,500.

| Elemental analysis | C | H | O |
| --- | --- | --- | --- |
| Calculated | 81.67 | 10.36 | 7.96 |
| Found | 81.66 | 10.38 | 8.20 |

The present invention also relates to, as a medicine, the unsaturated camphor derivatives of formula I, their isomers and their salts as defined above.

These compounds exhibit excellent activity in the ornithine decarboxylase inhibition test after induction by "tape stripping" the body of a nude rat. This test is considered a measure of retinoid activity on cellular proliferation phenomena.

They also exhibit increased activity in the differentiation test of $F_9$ embryonic terato-carcinoma cells. (Cancer Research 43, page 5268, 1983)

These compounds are particularly appropriate for the treatment of diseases linked to keratinization disorders (differentiation, proliferation, for example, of epithelial cells) as well as dermatological disorders or others with inflammatory components, principally:

ordinary acne, comedonian or polymorphic, solar senile acne, and professional or medicine-induced acnes, extensive and/or severe forms of psoriasis, and other keratinization problems, in particular ichthyosis and ichthyosislike states, Darier's disease, Palmo-plantar keratodermatosis, leukoplasia and leukoplasia-like states, lichen, all dermatological proliferations whether benign or malignant, severe or extensive.

They also have an action on certain rheumatoid ailments, in particular psoriatic rheumatism.

The present invention thus also relates to medicinal compositions containing at least one compound of formula I defined above.

The present invention further relates to a new medicinal composition, intended principally for the treatment of the above-mentioned ailments, characterized by the fact that it includes, in a pharmaceutically acceptable vehicle, at least one compound of formula I.

Besides the irritation test done on rabbits has shown that the compounds of formula I were less irritating than retinoic acid.

Compounds in accordance with the present invention are generally administered on a dialy basis of about 2 μg to 5 mg/kg and preferably from 10 μg to 2 mg/kg.

As a vehicle for the compositions, any conventional vehicle can be employed, the active compound being found either in the soluble state or in the dispersed state in said vehicle.

The compositions can be administred enterally, parenterally or topically.

Enterally, the medicines can be provided in the form of tablets, capsules, pills, syrups, suspensions, solutions, powders, granulars or emulsions.

Parenterally, the compositions can be provided in the form of solutions or suspensions for perfusion or for injection.

The pharmaceutical composition based on the compounds of the present invention provided in a form capable of being topically applied are in this case liniments, ointments, powders, stamps or pads impregnated with tinctures, creams, solutions, lotions, gels, sprays or even suspensions.

In accordance with this embodiment, the compositions for topical application contain preferably from 0.0001 to about 5 percent by weight of the compound of formula I.

The topically applied compositions can be provided either in anhydrous form or in aqueous form depending on clinical requirements and may contain other components.

These topically applied compositions such as dermal gels and creams are particularly intended for the local treatment of acne, common acne, solar acne and professional or medicine-induced acne as well as for keratinization disorders, in particular forms of parakeratosis, hyperkeratosis and diskeratosis.

In this type of treatment undesirable side effects have not been observed, the compositions generally being well tolerated by the patients.

In a general fashion, it is recommended that the application be carried out daily on the lesions by a massaging action so as to facilitate the penetration of the product.

The treatment must be followed in accordance with this regimen or one can increase the frequency of application to twice daily in the absence of any local reaction.

The duration of the treatment is generally several weeks, the first signs of improvement appearing toward the 6th week of treatment and continuing up to the end of the treatment, i.e. about the 12th or 14th week. After this treatment period, a rate of at least one daily application, the maintenance treatment consists in two or three applications per week.

Formula I compounds as defined above also have an application in the field of cosmetics, in particular for capillary and bodily hygiene and notably against acne, for promoting hair growth and preventing hair fall, for combatting the oily or greasy appearance of the skin or hair, or for the protection against the ill-effects of sun exposure, or to combat the skin's physiological dryness.

The present invention then also relates to a cosmetic composition containing in a cosmetically acceptable vehicle at least one compound of formula I, this composition being provided principally in the form of a lotion, gel, soap or shampoo.

The concentration of the compound(s) of formula I in these cosmetic compositions is between 0.0005 and 2 percent by weight and preferably between 0.01 and 1 percent by weight based on the total weight of the composition.

The medicinal and cosmetic compositions according to the present invention can also contain inert additives or even pharmacodynamically or cosmetically active additives such as, principally moisturizing agents such as thiamorpholinone and its derivatives or urea, antiseborrheric agents such as S-carboxymethyl cysteine, S-benzyl cysteamine and their derivatives, tioxolone, antibiotics such as erythromycin, neomycin and the tetracyclines, agents promoting hair growth such as "Minoxidil" (2,4-diamino-6-piperidino-3-pyrimidine oxide) and its derivatives, anthralin and its derivatives, diazoxide, phenytoin and oxapropanium iodide, steroid and non-steroid anti-inflammatory agents, carotenoids and principally, β-carotene, antipsoriasic agents such as anthralin and its derivatives, 5,8,11,14-eicosatetraynoic and 5,8,11-eicosatriynoic acids.

The compositions according to the present invention can also contain flavor-improving agents, preservatives, stabilizers, moisture regulating agents, pH regulating agents, osmotic pressure modifying agents, emulsifiers, UV-A and UV-B filters, antioxidants such as α-tocopherol, butylhydroxyanisole or butylhydroxytoluene.

The following non-limiting examples are given to illustrate the pharmaceutical and cosmetic compositions based on the unsaturated camphor derivatives of formula I of the present invention.

EXAMPLE A:

0.5 g insoluble compressed pill

| | |
|---|---|
| Compound of Example 13 | 0.050 g |
| Lactose | 0.082 g |
| Stearic acid | 0.003 g |
| Purified talc | 0.015 g |
| Sweetening agent, sufficient amount | |
| Dye, sufficient amount | |
| Rice starch, sufficient amount for | 0.500 g |

The compressed pills having 0.05 g of active component are obtained by direct dry compression of the mixture of the various components thereof.

These pills are administered at a rate of 2 to 4 pills each day in the treatment of psoriasis.

EXAMPLE B:

Capsule composition

| | |
|---|---|
| Compound of Example 1 (a1) | 0.050 g |
| Corn starch | 0.060 g |
| Lactose, sufficient amount for | 0.300 g |

This mixture is packaged in capsules made from gelatin, $TiO_2$ and a preservative.

1 to 3 capsules are administered daily in the treatment of acne, psoriasis or chronic polyarthritis.

EXAMPLE C:

Gel for topical application

| | |
|---|---|
| Compound of Example 2 | 0.050 g |
| Polyethylene glycol 400 | 80 g |
| Butylhydroxytoluene | 0.04 g |
| Ethanol, sufficient amount for | 100 g |

This gel is applied to skin exhibiting dermatosis or acne 1 to 3 times daily.

EXAMPLE D:

Emulsion for topical application

| | |
|---|---|
| Compound of Example 8 | 2 g |
| Benzylidene camphor | 4 g |
| Triglycerides of $C_8$ to $C_{12}$ fatty acids | 31 g |
| Glycerol monostearate | 6 g |
| Stearic acid | 2 g |
| Cetyl alcohol | 1.2 g |
| Lanolin | 4 g |
| Preservative | 0.3 g |
| Propanediol | 2 g |
| Triethanolamine | 0.5 g |
| Perfume | 0.4 g |
| Demineralized water, sufficient amount for | 100 g |

EXAMPLE E:

Gel for topical application

| | |
|---|---|
| Compound of Example 18(a) | 0.1 g |
| Ethanol | 43 g |
| α-tocopherol | 0.05 g |
| 20% aqueous solution of triethanol amine | 3.8 g |
| Water | 9.3 g |
| Propylene glycol, sufficient amount for | 100 g |

In this example the compound of Example 18(a) can be replaced by one of the compounds described in Examples 15, 17, 18(c) or 23.

What is claimed is:

1. An unsaturated camphor derivative having the formula wherein
the x bond is affixed in the meta or para position on the aromatic ring,
$R_1$ represents hydrogen,
$R_4$, $R_5$, $R_6$ and $R_7$ each independently represent hydrogen or methyl, and
$R_8$ represents (i)

$$-\overset{O}{\underset{\|}{C}}-OR_{15}$$

wherein $R_{15}$ represents hydrogen, alkyl or mono- or polyhydroxyalkyl or (ii)

$$-\overset{O}{\underset{\|}{C}}-N\overset{r'}{\underset{r''}{\diagdown}}$$

wherein r' represents hydrogen and r" represents alkyl, mono or polyhydroxyalkyl, phenyl, phenyl substituted by hydroxy, or r' and r" together with the nitrogen atom to which they are attached form a piperidine ring.

2. The derivative of claim 1 selected from the group consisting of
(1) [4-ethoxy carbonyl-3-methyl-1E,3E butadiene]-4'-yl-3E benzylidene camphor,
(2) [4-ethoxy carbonyl-3-methyl-1E,3Z-butadiene]-4'-yl-3E benzylidene camphor,
(3) [4-ethoxy carbonyl-3-methyl-1E,3E butadiene]-3'-yl-3E benzylidene camphor,
(4) [4-ethoxy carbonyl-1E,3E-butadiene]-4'-yl-3E benzylidene camphor,
(5) [4-ethoxy carbonyl-4-methyl-1E,3E-butadiene]-4'-yl-3E benzylidene camphor,
(6) [4-octadecyl oxycarbonyl-3-methyl-1E,3E-butadiene]-4'-yl-4E benzylidene camphor,
(7) [4-ethoxy carbonyl-1-methyl-1E,3E-butadiene]-4'-yl-3E benzylidene camphor,
(8) [4-ethoxy carbonyl-2-methyl-1E,3E butadiene]-4'-yl-3E benzylidene camphor,
(9) [4-carboxy-2-methyl-1E,3E butadiene]-4'-yl-3E benzylidene camphor,

(10) [4-carboxy-1E,3E butadiene-4'-yl-3E benzylidene camphor,
(11) [4-carboxy-3-methyl-1E,3E butadiene]-4'-yl-3E benzylidene camphor,
(12) [4-carboxy-3-methyl-1E,3E butadiene]-3'-yl-3E benzylidene camphor,
(13) [4-carboxy-3-methyl-1E,3Z butadiene]-4'-yl-3E benzylidene camphor,
(14) [4-carboxy-1-methyl-1E,3E butadiene]-4'-yl-3E benzylidene camphor,
(15) [4-carboxy-4-methyl-1E,3E butadiene]-4'-yl-3E benzylidene camphor,
(16) [4-N-ethyl carbamyl-3-methyl-1E,3E butadiene]-4'-yl-3E benzylidene camphor,
(17) [4-piperidyl carbonyl-3-methyl-1E,3E butadiene]-4'-yl-3E benzylidene camphor,
(18) [4-N-p-hydroxy phenyl carbamyl-4-methyl-1E,3E butadiene]-4'-yl-3E benzylidene camphor, and
(19) [2-N-hydroxy-4-ethyl carbamyl-3-methyl-1E,3E butadiene]-4'-yl-3E benzylidene camphor.

* * * * *